United States Patent
Niutta et al.

(10) Patent No.: US 7,255,834 B2
(45) Date of Patent: Aug. 14, 2007

(54) METHOD AND DEVICES FOR IMPROVING THE DYNAMIC FLASH COMBUSTION REACTION CONNECTED WITH GAS CHROMATOGRAPHY FOR THE ELEMENTAL ANALYSIS OF C H N S O

(75) Inventors: Stefano Boursier Niutta, Naples (IT); Leonardo Sisti, Redavalle (IT)

(73) Assignee: Eurovector S.p.A., Milan (IT)

( * ) Notice: Subject to any disclaimer, the term of this patent is extended or adjusted under 35 U.S.C. 154(b) by 590 days.

(21) Appl. No.: 10/302,306

(22) Filed: Nov. 22, 2002

(65) Prior Publication Data

US 2003/0077835 A1    Apr. 24, 2003

Related U.S. Application Data

(63) Continuation of application No. 09/369,998, filed on Aug. 6, 1999, now abandoned.

(30) Foreign Application Priority Data

Sep. 23, 1998  (IT) .......................... BS98A000068

(51) Int. Cl.
   *B32B 5/02* (2006.01)
(52) U.S. Cl. .............................. 422/78; 422/80; 422/88; 422/89; 422/94; 436/55; 436/155; 436/160
(58) Field of Classification Search ............... 422/68.1, 422/70, 99, 83, 89, 93, 100, 101, 102, 78, 422/80, 94; 436/55, 180, 155, 160
   See application file for complete search history.

(56) References Cited

U.S. PATENT DOCUMENTS

| | | | | |
|---|---|---|---|---|
| 4,234,315 A | * | 11/1980 | Scott | ........................... 436/115 |
| 4,401,763 A | * | 8/1983 | Itoh | ........................... 436/115 |
| 4,582,686 A | * | 4/1986 | Tsuji | ........................... 422/80 |
| 4,864,843 A | * | 9/1989 | Guieze et al. | ............. 73/23.38 |
| 5,019,517 A | * | 5/1991 | Coulson | ...................... 436/153 |
| 5,047,352 A | * | 9/1991 | Stetter et al. | ................ 436/181 |
| 5,424,217 A | * | 6/1995 | Benner et al. | .............. 436/123 |
| 5,550,062 A | * | 8/1996 | Wohltjen et al. | ............ 436/155 |
| 5,981,290 A | * | 11/1999 | Lyon et al. | .................. 436/157 |
| 6,130,095 A | * | 10/2000 | Shearer | ....................... 436/123 |

* cited by examiner

*Primary Examiner*—Jill Warden
*Assistant Examiner*—Dwayne K Handy
(74) *Attorney, Agent, or Firm*—Shoemaker and Mattare

(57) ABSTRACT

A method and device are provided for dynamic flash combustion reaction connected with gas chromatography for the elemental analysis of C H N S O in an automatic elemental analyzer. A combustion reactor is provided with a sampling device and an oxygen feed line. Controlled volumes of oxygen are admitted with the oxygen feed line into the combustion reactor depending on the sample for the complete combustion thereof. A pneumatic circuit is provided, in which the oxygen feed line converges and the pneumatic circuit creates a continuous flow of a carrier gas that is able to carry the oxygen to the reactor and the gases of the combustion through the reactor, then through a gas chromatographic analyzer, and after their separation, into a thermal conductivity detector. An electronic apparatus with a data processor is provided for controlling the process systems. The difference in the pressure of the gas upstream and downstream of a restrictor or restriction is determined. The electronic pressure regulator or flow regulator of the reference carrier gas and at least one carrier gas outlet valve, which is also used as purging, is inserted on this carrier gas reference line.

9 Claims, 3 Drawing Sheets

METHOD AND DEVICES FOR IMPROVING THE DYNAMIC FLASH COMBUSTION REACTION CONNECTED WITH GAS CHROMATOGRAPHY FOR THE ELEMENTAL ANALYSIS OF C H N S O

This is a Continuation of application Ser. No. 09/369,998 filed Aug. 6, 1999, now abandoned, and the entire disclosure of this prior application is considered to be part of the disclosure of the accompanying application and is hereby incorporated by reference therein.

FIELD OF THE INVENTION

The present invention pertains to the improvement of the flash dynamic combustion reaction connected with gas chromatography for carrying out the elemental analysis of C H N S O (carbon, hydrogen, nitrogen, sulfur and oxygen) in automatic elemental analyzers.

Specifically, the present invention pertains to a method, to devices, and to an arrangement of the devices in a pneumatic circuit under electronic control for improving the dynamic combustion reaction of a sample of material with the calculation of the optimal oxygen, as well as to the use of a novel system for metering the oxygen and to the ways of injecting the oxygen into a quartz, metal or ceramic reactor, which constitutes the initial phase of the process of analysis of C H N S O in solid and liquid samples of a wide variety of matrices.

BACKGROUND OF THE INVENTION

Automatic elemental analyzers are based on the principle of dynamic flash combustion of a sample followed by the elimination of the excess oxygen, the separation of the gases produced by the combustion, the passage of the gases produced through the packed column of a gas chromatographic column and subsequent quantitative determination with a thermal conductivity detector.

The accuracy and reproducibility of the elemental analysis is dependent on a number of factors, one of which is the completeness of the Combustion process. A minimum quantity of Oxygen is necessary to ensure complete combustion. The minimum quantity of Oxygen required depends on the nature of the sample matrix, the sample weight and the adjuvant to the combustion itself. The use of a large excess of Oxygen favors the completeness of the combustion process but results in undesirable consequences such as reduction in the lifetime of the expensive catalysts used in the elimination of the excess Oxygen downstream of the combustion, and an increase in the downtime of the instrument.

Furthermore, the optimization of the combustion process also relies on the capability to control the duration of the Oxygen admission. For identical Oxygen volume requirements, some sample matrices require a very sharp and short injection time, whilst others require that the Oxygen be administered at a slower rate.

The commercially available devices, to date, are based on the admission of fixed volumes of Oxygen from reservoirs of defined volumes, swept by a carrier gas. Whenever different volumes of Oxygen are required, the reservoirs must be manually exchanged, thus making the optimization of the oxygen quantity, labor intensive. Additionally none of these devices have the capability to control the rate of the Oxygen admission. These devices rely on the admission of a significant excess of Oxygen in order to endeavor to achieve complete combustion, however, even with a large excess of Oxygen, complete combustion is not necessarily achieved.

A recent application of the same applicant (Italian Patent Application BS97A000033) describes an arrangement which provides a facility to admit varying quantities of Oxygen. An Oxygen flow maintained constant by a mass flow controller is allowed to pass into the combustion chamber of the system, for periods of time which can be defined by the operator. In this arrangement, the admission of Oxygen occurs whilst the flow of carrier gas is interrupted. The flow of carrier gas is restored after the admission of Oxygen, hence these two gases flow alternately in the carrier line.

SUMMARY AND OBJECTS OF THE INVENTION

The present invention offers the means to admit an optimized volume of Oxygen and at the same time offers an independent control for the duration of the injection period of this volume.

The present invention results in an improved combustion process, adapted to the different types of sample matrices, sample weights and combustion adjuvant, and at the same time with a reduction of Oxygen excess, thus maximizing the lifetime of the catalysts.

Furthermore, the present invention allows the admission of the Oxygen gas into the carrier gas stream with no interruption of its flow, the geometry of the design was optimized in order to reduce to a minimum any disturbance that may be caused during the admission of Oxygen.

Disturbances to the carrier gas flow induce baseline instabilities of the signal from the thermal conductivity detector, which, if they coincide with the passage of a sample peak, cause inaccuracies of the analytical results.

The present invention pertains to both the analytical methods that use two separate reactors for the oxidation and reduction phase and those that perform the oxidation and the reduction in the same reactor with suitable temperature profiles, and it pertains to the use of quartz, metal or ceramic reactors which are heated in a suitable furnace or in furnaces at the usual temperatures ranging from 950° C. to 1,400° C. or at about 650-750° C. for the reduction.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
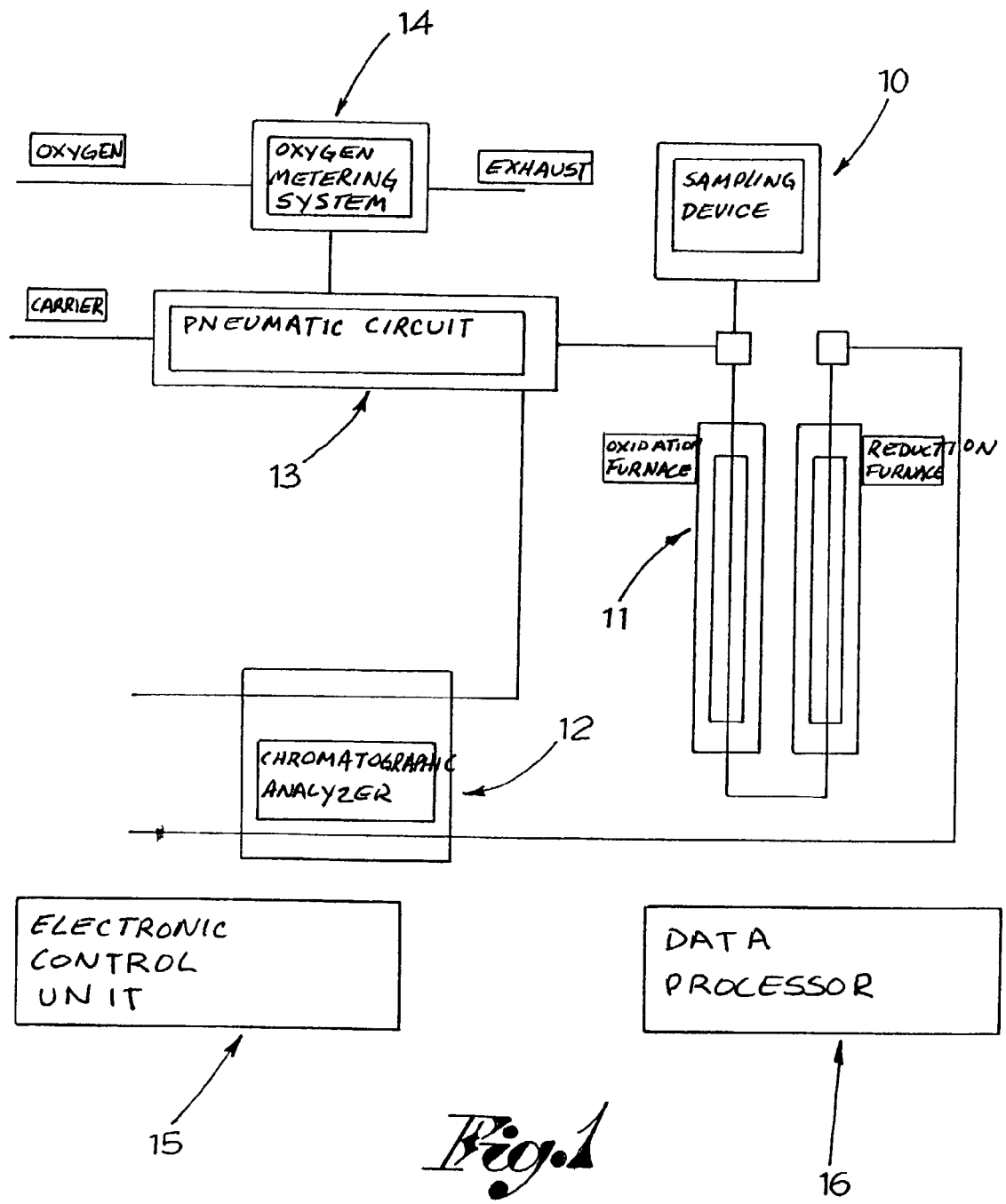
FIG. 1 is a schematic view of the components of a typical elemental analyzer of the type indicated above.

Referring to the drawings in particular, An elemental analyzer is an instrument intended for analyzing the elemental composition C H N S O in samples of solid or liquid materials. It comprises the following functional units (FIG. 1).

A sampling device 10 whose task is to introduce the sample into the combustion reactor.

A system 11 which consists of a furnace in which is accommodated a reaction tube usually made of quartz, metal, alumina or another material and brought to a temperature of about 950° C. to 1,400° C. for the combustion of the sample, which is thus converted into a gas mixture typically $N_2$, $CO_2$, $H_2O$, $SO_2$. A first reactor is provided with a catalytic bed which is able to facilitate and quantitatively complete the combustion reaction. The excess oxygen is eliminated by reduction by passage through a second copper-based catalytic bed accommodated in the bottom part of the first reactor or in a second reactor.

A gas chromatographic analyzer 12 for the time separation of the gases resulting from the combustion. The different gases are retained by the column filling of the gas chromatograph for different lengths of time, thus eluting from the column at different time intervals.

A pneumatic circuit 13, controlling the flow of carrier gas, usually Helium or Argon. The carrier gas entrains the combustion gases through the combustion and reduction reactors, through traps that may be present, through the chromatographic column and through the measuring cell of the thermal conductivity detector.

A stream of pure carrier gas also flows through the reference cell of the thermal conductivity detector, this flow acts as a balance for the measuring cell of the detector, it is also controlled from the pneumatic circuit 13.

A metering system 14 for the controlled admission of a preset amount of oxygen into the combustion system.

An electronic system 15 including a processor for controlling the operations of the various subsystems.

In particular, the Oxygen metering system 14 is a mechanism capable of providing known and preset amounts of Oxygen for the combustion process of the sample, according to the following criteria:

A sufficient quantity of Oxygen must be introduced into the combustion reactor in order to achieve a complete quantitative combustion at the combustion temperature of the reactor. An incomplete combustion would result in an inaccurate evaluation of the absolute and relative elemental composition of the sample.

A large excess of Oxygen must be avoided. The Oxygen, unused during the combustion process, has to be eliminated by expensive catalysts. These catalysts have to be replaced when they become exhausted. The intervention involves the manual removal of the reduction reactor, and forces the subsequent re-calibration of the operating conditions. It represents a significant downtime for the instrument.

The oxygen metering system 14, which is connected to the remaining pneumatic circuit 13, usually comprises: a tared-volume reservoir; a solenoid valve unit; two pressure and mass flow regulators; an electronic control unit.

The Oxygen metering system 14 operates in two stages. In a first stage, the reservoir is filled with Oxygen, in a second stage, the Oxygen is flushed out of the reservoir, by the carrier gas and is thus entrained by the carrier gas into the combustion reactor. The two stages are controlled by the electronic control unit.

Figure 2:
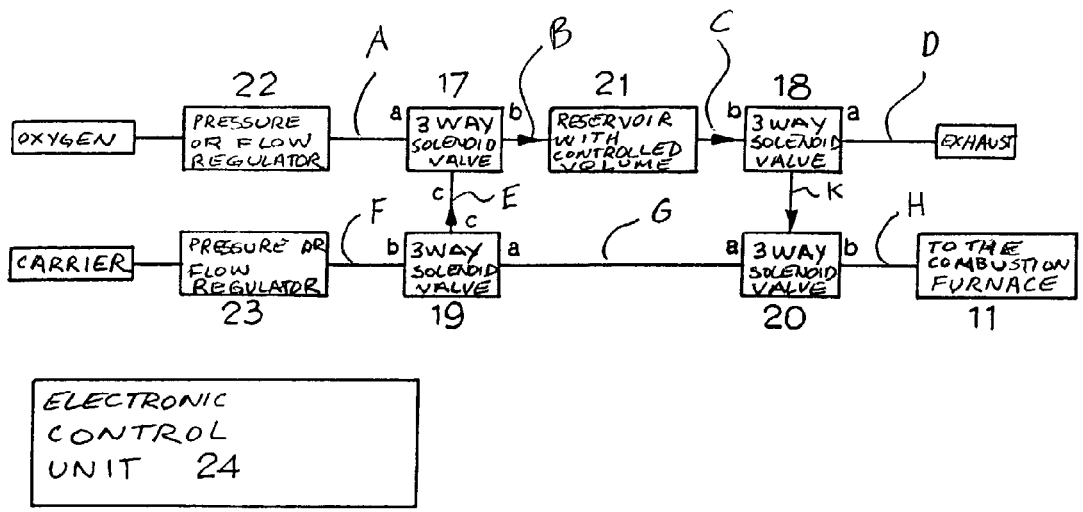
FIG. 2 is a schematic view of a typical system for metering the Oxygen in the typical analyzers of the type shown in FIG. 1.

FIG. 2 shows one possible embodiment of an Oxygen metering system, consisting of four three-way solenoid valves 17-20, a reservoir 21 with a preset volume, two pressure regulators 22, 23 and one electronic control unit 24.

The carrier gas and the Oxygen gas are both pressure or flow regulated by appropriate regulators 22 and 23, which may be either mechanical or electronic.

In a first stage, the solenoid valves 17 and 18 are switched to the state where conduits a, b, c and d are in connection thus allowing Oxygen gas to flow through the reservoir 21 and out to the vent port in pipe d. The reservoir 21 thus fills with Oxygen gas.

Simultaneously, solenoid valves 19 and 20 are switched to the state where conduits f, g and h are in connection, thus allowing the carrier gas to flow through to the combustion reactor.

During this stage, connecting conduits a and k are closed to the passage of any gas.

In a second stage, valves 17-20 are switched simultaneously to their other state such that conduits f, e, b, c, k and h are all in connections, thus allowing the carrier gas to flow through the pathway f, e, b, c, k and h. In particular, the carrier gas displaces the Oxygen gas previously accumulated in the reservoir 21, and entrains the Oxygen gas into the combustion furnace. During this stage, conduits a and d are closed to the flow of any gas, thus Oxygen gas is prevented from flowing into conduit b and no gas can vent out through conduit d."

It must be noted that if different amounts of Oxygen gas are required for the combustion, then the reservoir contained between conduits b and c has to be manually removed and exchanged for one of the appropriate volume.

For the analysis, the sample is weighed (from a few mg to a few hundred mg), then placed in a capsule which is carefully sealed by crushing the capsule material into a tight sphere. The capsule is placed on the sampling device and the weight for that particular sample is declared on the computer.

The Oxygen is allowed to fill the reservoir as previously described, and the carrier gas flows through the entire system, namely the combustion reactor, the reduction reactor, the chromatographic analyser, the measuring cell of the Thermal Conductivity Detector, then vents out to atmosphere.

Clean carrier gas also flows though the reference cell of the Thermal Conductivity Detector, it is necessary as a balance to the measuring cell and for initial calibration.

The analysis cycle starts with the initiation of the Oxygen flushing stage described above, the sampling device allows the sample to drop, under the action of gravity, into the combustion reactor at a time which coincides exactly with the arrival of the Oxygen gas at the combustion reactor. The sample contained within the closed capsule is flash combusted under the combined action of the exothermal reaction of the capsule, the presence of the admitted Oxygen and the presence of appropriate catalysts within the combustion reactor.

The gases produced by the combustion subsequently pass into the reducing catalytic bed, in which the excess oxygen is eliminated, and then they flow to the gas chromatographic analyzer, in which the separation of $N_{[2]}$, $CO_{[2]}$, $H_{[2]}O$, $SO_{[2]}$ and subsequent detection by the Thermal Conductivity Detector take place.

The Thermal Conductivity Detector signal is sent to the PC, which processes the data collected from the detector together with the previously declared weight of the sample and calculates its elemental composition.

The present system has the following limitations and drawbacks:

It does not offer any facility, other than the replacement of the reservoir, for optimization of the Oxygen volume, according to different sample matrices, sample weights and adjuvant to the combustion. Replacement of the reservoir is not a simple operation;

An excessive amount of Oxygen has to be used to guarantee complete combustion of the largest samples;

Inter-diffusion of the carrier gas and the Oxygen gas occurs, resulting in the mixing of these two gases, thus causing dilution of the Oxygen before it arrives at the site of combustion;

Oxygen gas vents continuously out the vent port, except for the short periods within each sample cycle when the valves are switched to the state whereby Oxygen gas is flushed out of the reservoir into the carrier gas line (as per stage 2 previously described);

There is no facility to control the rate of admission of the Oxygen gas into the combustion reactor.

Figure 3:
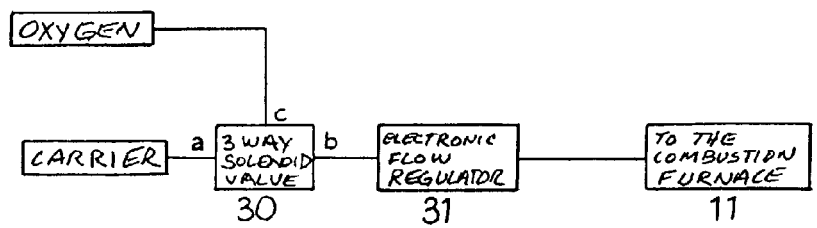
FIG. 3 is a schematic view of a system for metering the Oxygen as described in the above mentioned recent patent from the applicant.
Figure 3:
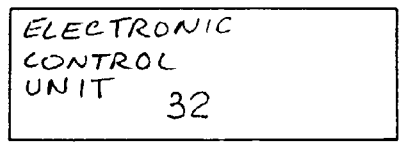

In the improved embodiment shown in FIG. 3 and described in the above mentioned previous patent by the same applicant, it is possible to control the quantity of Oxygen admitted into the combustion reactor, without the need to change any hardware.

Oxygen is admitted by means of a three-way solenoid valve 30. In one state of the valve, conduits a and b are in connection thus allowing the carrier gas to flow to the combustion reactor, in the other state of the valve, conduits c and b are in connection thus allowing Oxygen gas to flow to the combustion reactor whilst the carrier gas flow is interrupted. The flow of both gases are regulated by the electronic mass flow controller 31. This arrangement allows for the optimization of the volume of Oxygen according to the nature of the sample matrix, the weight of the sample and the adjuvant to the combustion. The volume of Oxygen admitted is directly proportional to the length of time that valve 30 remains in the 'Oxygen admit' state.

This novel method prevents admission of large excesses of Oxygen gas into the combustion reactor, however it suffers from the following limitations:

It does not offer the facility to control the rate of admission of the Oxygen gas into the combustion reactor;

The carrier gas flow is interrupted during the admission of the Oxygen into the system, because the three-way valve, in the 'Oxygen admit state', closes the passage of gas between pipes a and b. When the valve is switched to its other state and the carrier gas is re-admitted into the system, the flow regulator is not able to immediately restore constancy of flow in the entire analytical circuit. The perturbation of the carrier gas flow causes a disturbance to the baseline of the signal from the thermal conductivity detector. The recovery time is sufficiently long that the sample peaks eluting from the chromatographic column pass through the measuring cell of the detector before the baseline signal has been able to stabilize to its previous level. The electronic mass flow regulator is capable of immediately restoring the flow conditions in its immediate vicinity, but it cannot immediately restore the flow conditions in the entire analytical circuit. This effect compromises the analytical accuracy of the data for N and C.

The Oxygen which reaches the combustion reactor shows a higher dilution profile than the first system described, thus making the combustion process less efficient.

The present invention provides a novel method of arranging the valves, the electronic pressure regulators and the electronic mass flow meter, and in addition of supplying an Oxygen pathway through a restrictor, all of which are integral parts of the invention. The preferred embodiment of the invention provides the means to optimize the volume of Oxygen admitted into the combustion reactor and also to independently control its rate of admission. Oxygen is injected into the carrier gas without interruption to its flow, therefore the system does not suffer from the disadvantages previously described. Furthermore the geometry of the arrangement has been carefully designed to minimize inter-diffusion of the carrier gas and the Oxygen, thus minimizing dilution of the oxygen gas and offering the highest combustion efficiency.

These advantages apply with all reactor types, irrespective of their material and the temperature profile of their operation.

Figure 4:
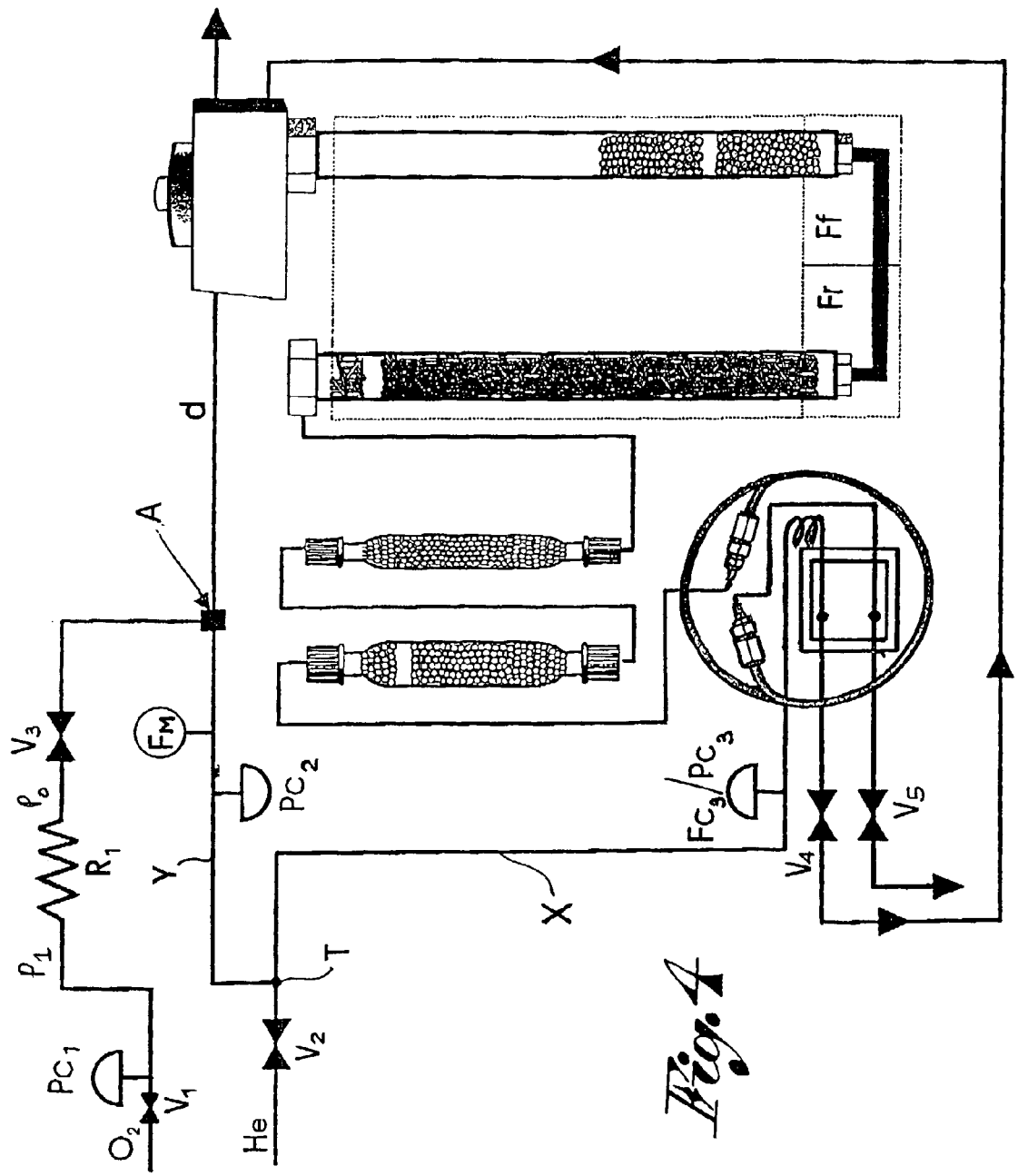
FIG. 4 is a schematic view of the system for metering the oxygen according to the present invention.

The preferred embodiment of the invention is shown in FIG. 4, where:.

| | |
|---|---|
| $V_1 =$ | Valve for admission of Oxygen |
| $V_2 =$ | Valve for admission of the carrier gas |
| $PC_1 =$ | Electronic Pressure Regulator for Oxygen |
| $R_1 =$ | Calibrated Restrictor |
| $V_3 =$ | Valve for injecting Oxygen into the carrier gas |
| T = | T junction for the division of the carrier gas into the reference line (X side) and sample line (Y side) |
| $PC_2 =$ | Electronic Pressure Regulator for the Carrier gas in the sample line |
| FM = | Electronic Flow meter for the carrier gas flow in the sample line |
| A = | T-junction between the Oxygen line and the carrier gas line |
| $FC_3/PC_3 =$ | Electronic Flow or Pressure Regulator for the reference carrier gas |
| V4 = | Valve for the reference carrier gas flowing subsequently into the sampling device and used as a purge. |
| $V_5 =$ | Valve for the sample carrier gas |
| Ff = | Front reactor (Combustion reactor) |
| Fr = | Rear reactor (reduction reactor) |

In the carrier gas circuit: The carrier gas, defined as Helium (He) for the purpose of the diagram, is admitted into the system via valve $V_2$. It divides into two lines at the point labelled T, one reference flow labeled X and one sample flow labeled Y. On the reference side, He is controlled by either an electronic mass flow regulator $FC_3$ or an electronic pressure regulator $PC_3$. The reference Helium passes through the reference cell of the Thermal Conductivity detector. It is then used as a means to purge the sampling device. On the sample side Y, He is regulated by a pressure regulator $PC_2$, resulting in a constant flow that is measured by the mass flow meter FM. Helium flows through the entire sample circuit and vents to atmosphere at the outlet of valve $V_5$.

In the Oxygen circuit:

Pure Oxygen gas is admitted into the system by the opening of valve $V_1$. The flow of Oxygen is regulated by means of a calibrated restrictor R, Using Poiseuille's equation, the Oxygen Flow (F) is given by:

$$F = \frac{\pi D^4}{256 \eta L} \cdot \frac{(P_1^2 - P_0^2)}{P_0}$$

In which:
D=diameter of the restrictor
L=length of the restrictor
η=viscosity of the gas
$P_1$=Pressure upstream of the restrictor
$P_0$=Pressure downstream of the restrictor.

In this equation, D, L and η are constant and Poiseuille's equation is simplified to:

$$F = K \cdot \frac{(P_1^2 - P_0^2)}{P_0}$$

$P_1$-$P_2$ represents the pressure drop across the restrictor, thereafter referred to as ΔP.

The electronic mass flow meter FM arranged in the carrier gas circuit provides a reading of the real mass flow for the carrier gas.

Starting from the matrix of the sample, from the combustion adjuvant and from the weight of the sample, it is possible to determine the theoretical amount of oxygen and to proceed, by means of automatic routines, with the optimal determination of the amounts and times in relation to the convergence of the analytical results obtained.

From the automatic calculation of the Oxygen flow through Restrictor R, using the Poiseuille equation, the instrument processor defines the length of time for which valve $V_3$ remains open to allow the introduction of the desired volume of Oxygen gas into the carrier gas.

It is thus possible to request the duration of the period of injection of a particular volume of Oxygen. For a fixed volume of Oxygen, if a short injection period is required, then by declaring a higher value for ΔP, the processor will automatically reduce the duration of the opening of Valve $V_3$, and we obtain a sharp and short injection of the said volume of Oxygen.

Oxygen is admitted into the carrier gas without interrupting its flow, the carrier gas flow can be visualized on the mass flow meter FM.

Furthermore, upon the closure of valve $V_3$, at the end of the Oxygen admission period, a disturbance of the flow of carrier gas is observed at the Mass flow meter. But it is also observed that the restoration of flow stability is very rapid, due to the nature of the regulating device, namely a pressure regulator. Stabilization of the carrier gas flow is complete before any sample peak arrives at the Thermal Conductivity Detector, thus providing a complete recovery of the baseline level which ensures total integrity of the sample data, and yields accurate and reproducible results.

While a specific embodiment of the invention has been shown and described in detail to illustrate the application of the principles of the invention, it will be understood that the invention may be embodied otherwise without departing from such principles.

What is claimed is:

1. A method for controlling oxygen flow during elemental analysis, the method comprising the steps of
providing a combustion reactor;
providing a gas chromatographic analyzer connected to said combustion reactor;
providing a pneumatic circuit connected to said combustion reactor and to said gas chromatographic analyzer;
passing a carrier gas through said pneumatic circuit, first through said combustion reactor and then to said gas chromatographic analyzer;
providing an oxygen feed line connected to said pneumatic circuit at an injection point upstream of said combustion reactor, said oxygen feed line including a restriction arranged upstream of said injection point;
measuring pressure in said oxygen feed line upstream and downstream of said restriction;
feeding oxygen from said oxygen feed line into said pneumatic circuit; and
adjusting one of an amount and a duration of the oxygen fed to said pneumatic circuit by adjusting said pressure upstream and downstream of said restriction.

2. A method in accordance with claim 1, wherein:
said adjusting of said pressure upstream and downstream of said restriction is performed to provide for an independent selection of the oxygen volumes and of the injection times, according to which an identical volume of oxygen can be injected for a different duration of time.

3. A method in accordance with claim 1, wherein:
said adjusting of said one of said amount and duration includes adjusting a length of time of said feeding of oxygen.

4. An elemental analyzer system comprising:
a combustion reactor;
a gas chromatographic analyzer connected to said combustion reactor;
a pneumatic circuit connected to said combustion reactor, said pneumatic circuit passing a carrier gas through said combustion reactor and to said gas chromatographic analyzer;
an oxygen feed line connected to said pneumatic circuit at an injection point upstream of said combustion reactor;
a restriction, in said oxygen feed line arranged upstream of said injection point; and
a processor for adjusting one of an amount and a duration of the oxygen fed to said pneumatic circuit by adjusting pressure upstream and downstream of said restriction.

5. An elemental analyzer system in accordance with claim 4, wherein:
said processor regulates based on a measurement of differences in said pressure upstream and downstream of said restriction, said processor varying said difference in pressure at said restriction for an independent selection of the amount of oxygen and the duration, according to which an identical volume of oxygen can be injected for a different duration of time.

6. An elemental analyzer system in accordance with claim 4, wherein:
said processor also adjusts a length of time of said feeding of oxygen.

7. An elemental analyzer system in accordance with claim 4, wherein:
a sample is placed in said combustion reactor;
a theoretical amount of oxygen for substantially complete combustion of the sample is determined based on a matrix of the sample, a combustion adjuvant of the sample and from a weight of the sample;
said processor proceeds with said adjusting of said one of said amount and said duration of said oxygen from said theoretical amount;
said processor obtains analytical results from said adjusting of said one of said amounts and duration of oxygen;

said processor determines optimal said amounts and durations of said oxygen by convergence of said analytical results.

8. The method for improving dynamic flash combustion reaction that is connected with gas chromatography for elemental analysis of C H N S O in an automatic elemental analyzer, the method comprising the steps of providing at least one combustion reactor;

providing a sampling device;

introducing a sample of material into the combustion reactor with the sampling device;

providing an oxygen feed line with a restriction;

admitting controlled volumes of oxygen with the oxygen feed line into the combustion reactor depending on the sample for the complete combustion thereof;

providing a pneumatic circuit, in which the oxygen feed line converges and creating a continuous flow of a carrier gas that is able to carry the oxygen to the reactor and the gases of the combustion through the reactor, then through a gas chromatographic analyzer, and after their separation, into a thermal conductivity detector;

providing an electronic apparatus with a data processor for regulating the oxygen flow based on a measurement of the differences in pressure upstream and downstream of said restriction; and injecting an identical volume of oxygen for a different duration of time by varying said pressure upstream and downstream of said restriction for an independent selection of the oxygen volumes and of the injection times.

9. A device for metering the oxygen in an elemental analyzer of the gases of the combustion of a sample a combustion reactor;

a sampling device, a sample of material being introduced into the combustion reactor with the sampling device;

an oxygen feed line for admitting controlled volumes of oxygen into the combustion reactor depending on the sample for the complete combustion thereof;

a pneumatic circuit, in which the oxygen feed line converges and creates a continuous flow of a carrier gas that is able to carry the oxygen to the reactor and the gases of the combustion through the reactor, then through a gas chromatographic analyzer, and after their separation, into a thermal conductivity detector;

an electronic apparatus with a data processor for controlling the process;

a restriction in said oxygen support line;

an admission valve upstream of said restriction;

an injection valve downstream of the said restriction;

a carrier line for a carrier gas, having an admission valve, and being divided by means of a T junction, into a reference line and into a sample line, said oxygen feed line with said restriction meets said sample line;

an electronic oxygen pressure regulator associated with said oxygen feed line upstream of said restriction;

an electronic carrier gas pressure regulator on a carrier gas sample line;

an electronic flow meter, for the measurement of the cater gas flow in the sample line;

an electronic pressure regulator or an electronic flow regulator for the carrier gas in the reference line; and a carrier gas outlet valve included in the reference line, for the control of the reference carrier gas, which is also used for purging the sampling device.

* * * * *